(12) United States Patent
Deak et al.

(10) Patent No.: US 11,408,949 B2
(45) Date of Patent: Aug. 9, 2022

(54) MAGNETORESISTIVE HYDROGEN SENSOR AND SENSING METHOD THEREOF

(71) Applicant: MultiDimension Technology Co., Ltd., Zhangjiagang (CN)

(72) Inventors: James Geza Deak, Zhangjiagang (CN); Xuanzuo Liu, Zhangjiagang (CN)

(73) Assignee: MultiDimension Technology Co., Ltd., Zhangjiagang (CN)

( * ) Notice: Subject to any disclaimer, the term of this patent is extended or adjusted under 35 U.S.C. 154(b) by 0 days.

(21) Appl. No.: 17/309,266

(22) PCT Filed: Nov. 13, 2019

(86) PCT No.: PCT/CN2019/118051
§ 371 (c)(1),
(2) Date: May 13, 2021

(87) PCT Pub. No.: WO2020/103740
PCT Pub. Date: May 28, 2020

(65) Prior Publication Data
US 2022/0011385 A1 Jan. 13, 2022

(30) Foreign Application Priority Data
Nov. 19, 2018 (CN) .......................... 201811377334.5

(51) Int. Cl.
*G01R 33/09* (2006.01)
*G01N 27/04* (2006.01)

(52) U.S. Cl.
CPC ......... *G01R 33/091* (2013.01); *G01N 27/045* (2013.01); *G01R 33/093* (2013.01)

(58) Field of Classification Search
CPC ............................. G01R 33/093; G01R 33/091
See application file for complete search history.

(56) References Cited

U.S. PATENT DOCUMENTS

| 8,933,523 B2 | 1/2015 | Deak et al. |
| 9,817,084 B2 | 11/2017 | Deak |

(Continued)

FOREIGN PATENT DOCUMENTS

| CN | 102621504 A | 8/2012 |
| CN | 103267955 | 8/2013 |

(Continued)

OTHER PUBLICATIONS

"International Application No. PCT/CN2019/118051, International Search Report and Written Opinion dated Feb. 12, 2020", (dated Feb. 12, 2020), 13 pgs.

*Primary Examiner* — Alesa Allgood
(74) *Attorney, Agent, or Firm* — Schwegman Lundberg & Woessner, P.A.

(57) ABSTRACT

A magnetoresistive hydrogen sensor and sensing method thereof, wherein the hydrogen sensor comprises a substrate located in an X-Y plane, magnetoresistive sensing units and magnetoresistive reference units located on the substrate. The magnetoresistive sensing units are electrically connected to form a sensing arm, and the magnetoresistive reference units are electrically connected to form a reference arm. The sensing arm and the reference arm are electrically interconnected to form a referenced bridge structure. The magnetoresistive sensing units and the magnetoresistive reference units may be AMR units having the same magnetic multilayer thin film structure, GMR spin valves, or GMR multilayer film stacks having the same magnetic multilayer thin film structure. The magnetoresistive sensing units and the magnetoresistive reference units are respectively covered with a Pd layer, and a passivating insulation layer is deposited over the Pd layer of the magnetoresistive reference units. The magnetic multilayer thin film structure is (Continued)

made into a serpentine strip circuit by a semiconductor micromachining process. The hydrogen detecting method comprises placing the hydrogen sensor in a gas environment containing hydrogen, the Pd layers covering in the magnetoresistive sensing units absorb hydrogen to change the perpendicular magnetic anisotropy of ferromagnetic layers in the magnetic multilayer thin film structures of the magnetoresistance sensing units, which makes the magnetic moment of the ferromagnetic layer rotate to produce a change in the magnetoresistance value that correlates to the hydrogen concentration. The resulting change of the magnetoresistance value changes the output voltage value of the referenced bridge structure, and this change of the output voltage value of the referenced bridge structure is used to measure the hydrogen concentration.

9 Claims, 8 Drawing Sheets

(56) References Cited

U.S. PATENT DOCUMENTS

| | | | |
|---|---|---|---|
| 10,473,449 | B2 | 11/2019 | Deak et al. |
| 2002/0017126 | A1 | 2/2002 | Dimeo et al. |
| 2014/0054733 | A1 | 2/2014 | Deak et al. |
| 2016/0109535 | A1 | 4/2016 | Deak |
| 2016/0313412 | A1 | 10/2016 | Li et al. |
| 2017/0268864 | A1 | 9/2017 | Deak et al. |

FOREIGN PATENT DOCUMENTS

| | | |
|---|---|---|
| CN | 104197828 | 12/2014 |
| CN | 104900801 A | 9/2015 |
| CN | 108169185 A | 6/2018 |
| CN | 207586166 U | 7/2018 |
| CN | 109283228 A | 1/2019 |
| CN | 209400462 U | 9/2019 |
| WO | WO-2020103740 A1 | 5/2020 | ly
MAGNETORESISTIVE HYDROGEN SENSOR AND SENSING METHOD THEREOF

PRIORITY CLAIM TO RELATED APPLICATIONS

This application is a U.S. national stage filing under 35 U.S.C. § 371 from International Application No. PCT/CN2019/118051, filed on 13 Nov. 2019, and published as WO2020/103740 on 28 May 2020, which claims the benefit under 35 U.S.C. 119 to Chinese Application No. 201811377334.5, filed on 19 Nov. 2018, the benefit of priority of each of which is claimed herein, and which applications and publication are hereby incorporated herein by reference in their entirety.

TECHNICAL FIELD

The present disclosure relates to the field of gas sensor technologies, and in particular to a magnetoresistive hydrogen sensor and a method for detecting hydrogen using the same.

BACKGROUND

As a replacement for fossil fuels, or as a renewable energy without hazardous emissions, hydrogen has attracted increasingly more worldwide attention and has been developed rapidly in recent years. At present, all major economic entities in the world, such as the United States, the European Union, and Japan, are researching hydrogen for use as fuel for future vehicles and households. Companies such as Toyota have begun to design and produce hydrogen-fueled vehicles.

Hydrogen cannot be detected by human sense organs, and it is unfortunately highly flammable and explosive. The flammability threshold of hydrogen in air is about 4%. As such, a reliable and highly sensitive hydrogen sensor is required to ensure the safety of hydrogen fueled equipment. There are many types of conventional hydrogen sensors. For example, patent CN108169185A discloses an optical sensor based on surface plasmon resonance, which monitors a peak position and intensity change of a surface plasmon resonance peak in a spectrum of light reflected from the surface of a metal nanorod array using a spectrograph, thereby achieving real-time sensing of hydrogen in an environment. The disadvantage is that the optical measurement method is too complex and a transparent test vessel is required. For another example, patent CN207586166U discloses a fuel cell-based hydrogen sensor, which detects hydrogen concentration, based on effects of heat generated by an exothermic chemical reaction between hydrogen and oxygen on Pt on the resonance frequency of a crystal substrate, by monitoring the frequency difference before and after the reaction. The disadvantage is that the range of detectable hydrogen concentration is small (only below 4%).

In the prior art, the most mature resistive thin-film hydrogen sensor is a Pd/Pd alloy thin-film resistive sensor based on a principle that Pd is a good absorber of hydrogen. Pd is highly selective for hydrogen absorption, this absorption is reversible, and palladium hydride will be formed after absorption. During the absorption, the resistivity of Pd has changed, and the purpose of detecting hydrogen concentration may be achieved by detecting the resistance value change of Pd. The main disadvantages of such hydrogen sensors are mainly low sensitivity and long response time.

SUMMARY OF THE INVENTION

In order to solve the above technological limitations, the present disclosure presents a magnetoresistive hydrogen sensor and a method for detecting hydrogen using the same based on a working principle that after a Pd covering layer absorbs hydrogen, on the one hand, perpendicular magnetic anisotropy induced in an adjacent ferromagnetic layer below is changed thus producing a magnetoresistance change that positively correlates to the hydrogen concentration in an external environment; on the other hand, the dissolution of hydrogen atoms diffused into Pd thin-film lattices will cause the resistance of the Pd covering layer to change; as a result of the combined action of these two effects high-sensitivity sensing of hydrogen concentration may be achieved.

The present disclosure is implemented using the following technical solutions:

In a first aspect, an embodiment of the present disclosure provides a magnetoresistive hydrogen sensor, including:

a substrate located on an X-Y plane;

magnetoresistive sensing units and magnetoresistive reference units located on the substrate, the magnetoresistive sensing units being electrically connected to form a sensing arm, the magnetoresistive reference units being electrically connected to form a reference arm, the sensing arm and the reference arm being electrically interconnected to form a referenced bridge structure; wherein the magnetoresistive sensing units and the magnetoresistive reference units are anisotropy magneto resistance (AMR) units having a same magnetic multilayer thin film structure, or giant magneto resistance (GMR) units having a same magnetic multilayer thin film structure; the magnetoresistive sensing units and the magnetoresistive reference units are respectively covered with a Pd layer, and a passivating insulation layer further covers over the Pd layer covering the magnetoresistive reference units;

the magnetic multilayer thin film structure is made into a serpentine strip circuit by a semiconductor micromachining process, a parallel line segment of the serpentine strip circuit follows an X direction, a corner of the serpentine strip circuit follows a Y direction, a gap is formed between adjacent parallel line segments of the serpentine strip circuit, a long axis of the gap follows the X direction, a short axis of the gap follows the Y direction; and the semiconductor micromachining process includes, but is not limited to, a photoetching technology and an ion etching technology;

wherein the Pd layer covering the magnetoresistive sensing units absorbs hydrogen to change magnetic anisotropy of ferromagnetic layers in the magnetoresistive sensing units; the passivating insulation layer isolates hydrogen to avoid changing magnetic anisotropy of ferromagnetic layers in the magnetoresistive reference units; and a hydrogen concentration is detected based on an output voltage value change of the referenced bridge structure before and after absorbing hydrogen.

Further, the magnetic multilayer thin film structure of the AMR unit includes from bottom to top: a seed layer and a composite intermediate layer; wherein the composite intermediate layer is [perpendicular magnetic anisotropy (PMA) interface layer/ferromagnetic layer]$_n$, n being an integer.

Further, when the GMR unit is of a GMR spin valve structure, the magnetic multilayer thin film structure includes from bottom to top: a seed layer, an antiferromagnetic layer, a PMA ferromagnetic layer, a buffer layer, a Cu spacer layer, a buffer layer, a ferromagnetic layer, a composite intermediate layer, and a Pd layer, or includes from top to bottom: a seed layer, a PMA interface layer, a PMA ferromagnetic layer, a buffer layer, a Cu spacer layer, a buffer layer, a ferromagnetic layer, and a composite intermediate layer; wherein the composite intermediate layer is [PMA interface layer/ferromagnetic layer]$_m$ being an integer; or when the GMR unit is a GMR multilayer film stack having interlayer antiferromagnetic coupling, the magnetic multilayer thin film structure comprises from bottom to top: a seed layer and a multi-film intermediate layer; wherein the multi-film intermediate layer is [ferromagnetic layer/nonmagnetic intermediate layer/ferromagnetic layer]$_p$, p being an integer.

Further, an easy axis of the ferromagnetic layer is perpendicular to an X-Y plane, a magnetic moment of the ferromagnetic layer deflects towards an adjacent Pd layer within an X-Z plane within an angle range of 10°-80°, and the ferromagnetic layer is made of a magnetostrictive material, including but not limited to one of single elements of Fe, Co, or Ni, or one of alloys of CoFe, NiFe, CoPt, CoPd, CoFeB, or NiFeCo.

Further, a block permanent magnet is provided below the substrate, and the block permanent magnet generates a magnetic field along a positive direction of a Z-axis; or, a thin-film permanent magnet is provided between the substrate and the referenced bridge structure, and the thin-film permanent magnet generates a magnetic field along the positive direction of the Z-axis; or a strip-shaped permanent magnet array is provided above or below the serpentine strip circuit, and the strip-shaped permanent magnet array includes a plurality of strip-shaped permanent magnets arranged between the gap between the parallel line segments of the serpentine strip circuit and generating a magnetic field along a positive direction of a Y-axis.

Further, the referenced bridge structure includes, but is not limited to a half-bridge structure, a full-bridge structure, or a quasi-bridge structure.

Further, a material of the substrate includes, but is not limited to, one of Si, SiO2, or fused silica, and a material of the passivating insulation layer includes, but is not limited to, one of photoresist, Al2O3, or SiN.

In the above technical solutions, a material of the PMA ferromagnetic layer includes, but is not limited to, one of Co or CoFeB, a material of the buffer layer includes, but is not limited to, one of Ta or Ru, and a material of the nonmagnetic intermediate layer includes, but is not limited to, one of Cu, Ru, Pd, Cr, Au, or Ag.

An embodiment of the present disclosure further presents a method for detecting a hydrogen concentration using the above magnetoresistive hydrogen sensor, including:

placing the hydrogen sensor in a hydrogen-containing gas environment, absorbing hydrogen by the Pd layer covering the magnetoresistive sensing units to change perpendicular magnetic anisotropy of the ferromagnetic layers in the magnetic multilayer thin film structures of the magnetoresistive sensing units, such that the magnetic moment of the ferromagnetic layer rotates to produce a magnetoresistance value change that positively correlates to the hydrogen concentration;

obtaining an output voltage value change of a bridge structure based on the magnetoresistance value change, and detecting the hydrogen concentration based on the output voltage value change of the bridge structure.

Compared with the prior art, the present disclosure has the following beneficial technical effects:

all bridge arms in embodiments of the present disclosure have a same response to an external magnetic field interference, and therefore the present disclosure is immune to external magnetic field interferences. As a bridge structure, the present disclosure has very favorable temperature compensation and high sensitivity, and has the advantages of small size, low power consumption, wide detection range of hydrogen concentration, and the like.

BRIEF DESCRIPTION OF THE DRAWINGS

After reading detailed description of non-limiting embodiments with reference to the following accompanying drawings, other features, objectives and advantages of the present disclosure will become more apparent.

REFERENCE NUMERALS

1—substrate, 2—magnetoresistive sensing unit, 3—magnetoresistive reference unit, 4—sensing arm, 5—reference arm, 6—bridge structure, 7—passivating insulation layer, 100—magnetic multilayer thin film structure, 11—seed layer, 12—PMA interface layer, 13—ferromagnetic layer, 14—Pd layer, 21—antiferromagnetic layer, 22—PMA ferromagnetic layer, 23—dispersion layer, 24—Cu spacer layer, 25—non-magnetic intermediate layer, 30—block permanent magnet, 40—thin-film permanent magnet, 50—strip-shaped permanent magnet array, A—magnetic multilayer thin film structure.

DETAILED DESCRIPTION

To make the objectives, technical solutions, and advantages of the present disclosure clearer, the technical solutions in embodiments of the present disclosure will be clearly and completely described below in conjunction with the accompanying drawings in the embodiments of the present disclosure. Apparently, the embodiments described below are a part, instead of all, of the embodiments of the present disclosure.

The present disclosure will be described in detail below with reference to the accompanying drawings and in combination with the embodiments.

Figure 1:
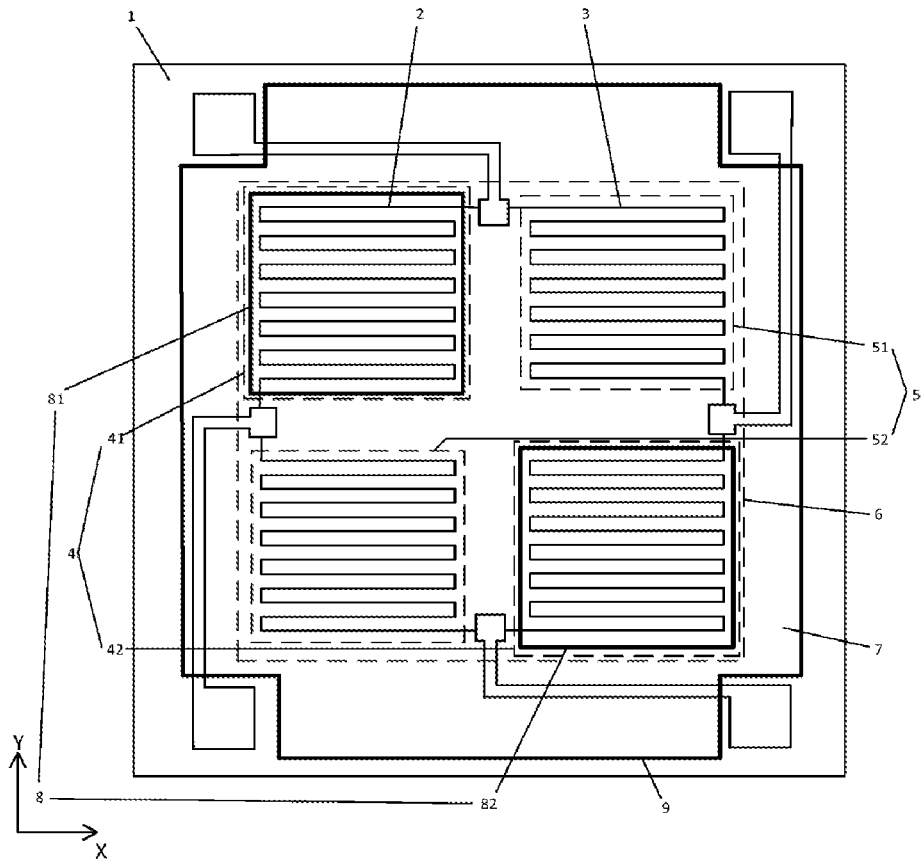
FIG. 1 is a schematic structural diagram of a magnetoresistive hydrogen sensor provided in an embodiment of the present disclosure.

FIG. 1 is a schematic structural diagram of a magnetoresistive hydrogen sensor provided in an embodiment of the present disclosure. As shown in FIG. 1, the magnetoresistive hydrogen sensor includes: a substrate 1 located on an X-Y plane;

magnetoresistive sensing units 2 and magnetoresistive reference units 3 located on the substrate 1, the magnetoresistive sensing units 2 being electrically connected to form a sensing arm 4, the magnetoresistive reference units 3 being electrically connected to form a reference arm 5, the sensing arm 4 and the reference arm 5 being electrically interconnected to form a referenced bridge structure 6; wherein the magnetoresistive sensing units 2 and the magnetoresistive reference units 3 are AMR units having a same magnetic multilayer thin film structure, or GMR units having a same magnetic multilayer thin film structure; the magnetoresistive sensing units 2 and the magnetoresistive reference units 3 are respectively covered with a Pd layer, and a passivating insulation layer 7 further covers over the Pd layer covering the magnetoresistive reference units 3.

The magnetic multilayer thin film structure is made into a serpentine strip circuit by a semiconductor micromachining process, a parallel line segment of the serpentine strip circuit follows an X direction, a corner of the serpentine strip circuit follows a Y direction, a gap is formed between adjacent parallel line segments of the serpentine strip circuit, a long axis of the gap follows the X direction, a short axis of the gap follows the Y direction; and the semiconductor micromachining process includes, but is not limited to, a photoetching technology and an ion etching technology. A current flows along the serpentine circuit within the X-Y plane.

The Pd layer covering the magnetoresistive sensing units 2 absorbs hydrogen to change magnetic anisotropy of ferromagnetic layers in the magnetoresistive sensing units 2; the passivating insulation layer 7 isolates hydrogen to avoid changing magnetic anisotropy of ferromagnetic layers in the magnetoresistive reference units 3; and a hydrogen concentration is detected based on an output voltage value change of the referenced bridge structure 6 before and after absorbing hydrogen.

Further, a material of the substrate 1 includes, but is not limited to, one of Si, SiO2, fused silica, or the like.

Further, as shown in FIG. 1, the sensing arm 4 and the reference arm 5 are interconnected to form a full-bridge structure, the sensing arm 4 includes a first sensing arm 41 and a second sensing arm 42, and the reference arm 5 includes a first reference arm 51 and a second reference arm 52. The sensing arm 4 and the reference arm 5 are electrically interconnected to form a referenced bridge structure 6.

The passivating insulation layer 7 further covers over the Pd layer covering the magnetoresistive reference units. A material of the passivating insulation layer 7 includes, but is not limited to, one of photoresist, Al2O3, or SiN.

Figure 2A:
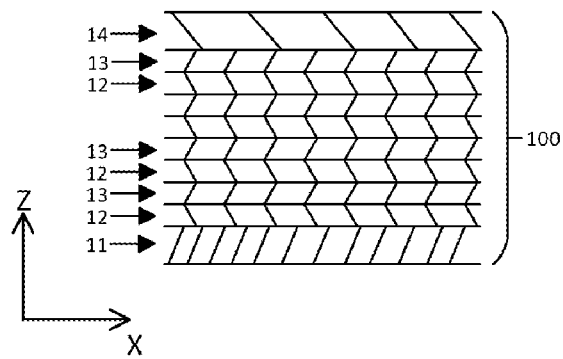
FIG. 2(a) is a schematic diagram of a magnetic multilayer thin film structure of an AMR unit provided in an embodiment of the present disclosure.

Specifically, FIG. 2(a) is a schematic diagram of a magnetic multilayer thin film structure of an AMR unit provided in an embodiment of the present disclosure. As shown in FIG. 2(a), the magnetic multilayer thin film structure 100 of the AMR unit includes from bottom to top: a seed layer 11, [PMA interface layer 12/ferromagnetic layer 13]$_n$, and a Pd layer 14, where n is an integer.

Figure 2B:
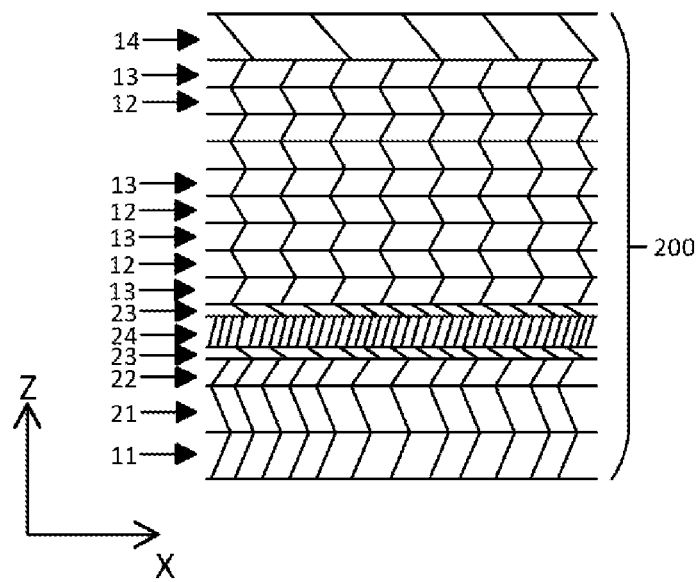
FIG. 2(b) is a schematic diagram of a magnetic multilayer thin film structure when a GMR unit is a GMR spin valve provided in an embodiment of the present disclosure.

Specifically, FIG. 2(b) is a schematic diagram of a magnetic multilayer thin film structure when a GMR unit is a GMR spin valve provided in an embodiment of the present disclosure. As shown in FIG. 2(b), the magnetic multilayer thin film structure 200 of the GMR spin valve includes from bottom to top: a seed layer 11, an antiferromagnetic layer 21, a PMA ferromagnetic layer 22, a buffer layer 23, a Cu spacer layer 24, a buffer layer 23, a ferromagnetic layer 13, [PMA interface layer 12/ferromagnetic layer 13]$_m$, and a Pd layer 14, where m is an integer.

Figure 2C:
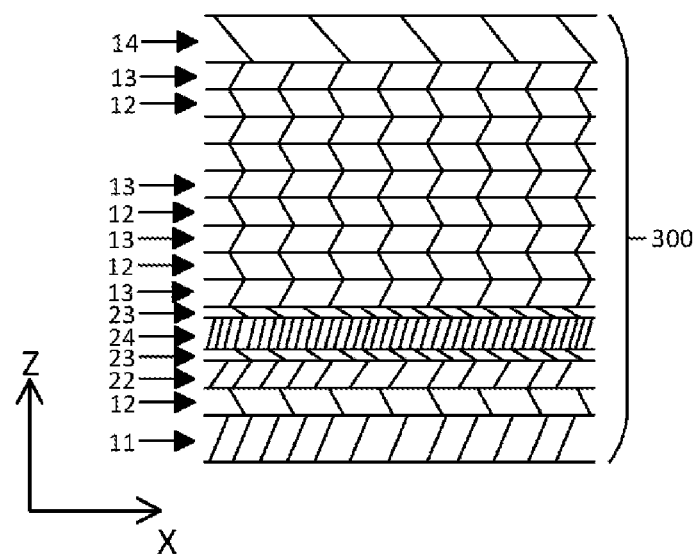
FIG. 2(c) is a schematic diagram of another magnetic multilayer thin film structure when the GMR unit is the GMR spin valve provided in an embodiment of the present disclosure.

Specifically, FIG. 2(c) is a schematic diagram of another magnetic multilayer thin film structure when the GMR unit is the GMR spin valve provided in an embodiment of the present disclosure. As shown in FIG. 2(c), another magnetic multilayer thin film structure 300 of the GMR spin valve includes from bottom to top: a seed layer 11, a PMA interface layer 12, a PMA ferromagnetic layer 22, a buffer layer 23, a Cu spacer layer 24, a buffer layer 23, a ferromagnetic layer 13, [PMA interface layer 12/ferromagnetic layer 13]k, and a Pd layer 14, where k is an integer.

Figure 2D:
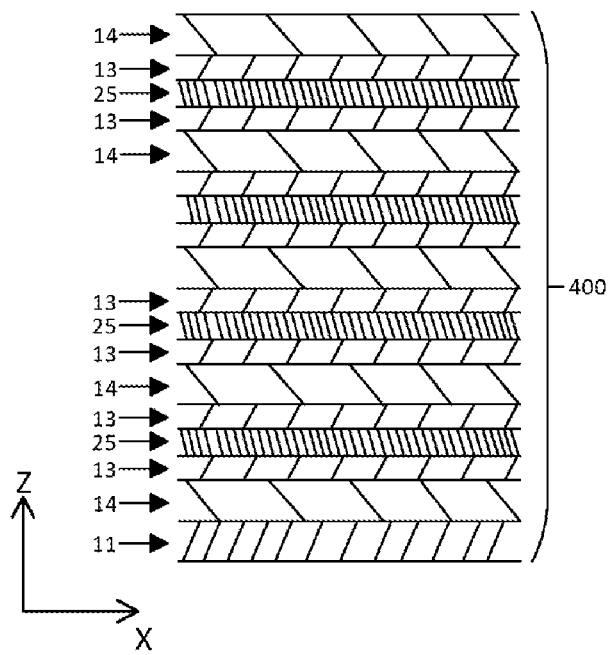
FIG. 2(d) is a schematic diagram of a magnetic multilayer thin film structure when the GMR unit is a GMR multilayer film stack having strong interlayer antiferromagnetic coupling provided in an embodiment of the present disclosure.

Specifically, FIG. 2(d) is a schematic diagram of a magnetic multilayer thin film structure when the GMR unit is a GMR multilayer film stack having strong interlayer antiferromagnetic coupling provided in an embodiment of the present disclosure. As shown in FIG. 2(d), the magnetic multilayer thin film structure 400 of the GMR multilayer film stack includes from bottom to top: a seed layer 11, [Pd layer 14/ferromagnetic layer 13/non-magnetic intermediate layer 25/ferromagnetic layer 13]$_p$, and a Pd layer 14, where p is an integer.

In this embodiment, the Pd layer 14 induces perpendicular magnetic anisotropy in the adjacent ferromagnetic layer 13. The Pd layer 14 absorbs hydrogen to change perpendicular magnetic anisotropy induced in the ferromagnetic layer 13, such that the magnetic moment of the ferromagnetic layer 13 rotates to produce a magnetoresistance change that positively correlates to the hydrogen concentration.

Specifically, a material of the seed layer 11 includes, but is not limited to, one of Ta or W. A material of the PMA interface layer 12 includes, but is not limited to, one of MgO, Pd, or Pt. A material of the passivating insulation layer 7 includes, but is not limited to, one of photoresist, $Al_2O_3$, or SiN.

A material of the PMA ferromagnetic layer 22 includes, but is not limited to, one of Co or CoFeB, a material of the buffer layer 23 includes, but is not limited to, one of Ta or Ru, and a material of the non-magnetic intermediate layer 25 includes, but is not limited to, one of Cu, Ru, Pd, Cr, Au, or Ag.

Figure 3:
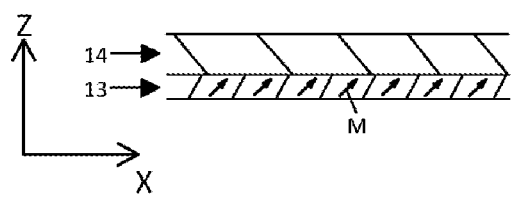
FIG. 3 is a schematic diagram of a magnetization direction of a ferromagnetic layer provided in an embodiment of the present disclosure.

Further, FIG. 3 is a schematic diagram of a magnetization direction of a ferromagnetic layer provided in an embodiment of the present disclosure. As shown in FIG. 3, an easy axis of the ferromagnetic layer 13 is perpendicular to an X-Y plane, and the Pd layer 14 induces perpendicular magnetic anisotropy in the ferromagnetic layer 13, such that a magnetic moment of the ferromagnetic layer 13 deflects towards an adjacent Pd layer 14 within an X-Z plane within an angle range of 10°-80°, and the ferromagnetic layer 13 is made of a magnetostrictive material, including but not limited to one of single elements of Fe, Co, or Ni, or one of alloys of CoFe, NiFe, CoPt, CoPd, CoFeB, or NiFeCo.

Further, a block permanent magnet is provided below the substrate 1, and the block permanent magnet generates a magnetic field along a positive direction of a Z-axis; or, a thin-film permanent magnet is provided between the substrate 1 and the referenced bridge structure 6, and the thin-film permanent magnet generates a magnetic field along the positive direction of the Z-axis; or a strip-shaped permanent magnet array is provided above or below the serpentine strip circuit, and the strip-shaped permanent magnet array includes a plurality of strip-shaped permanent magnets arranged between the gap between the parallel line segments of the serpentine strip circuit and generating a magnetic field along a positive direction of a Y-axis.

Figure 4A:
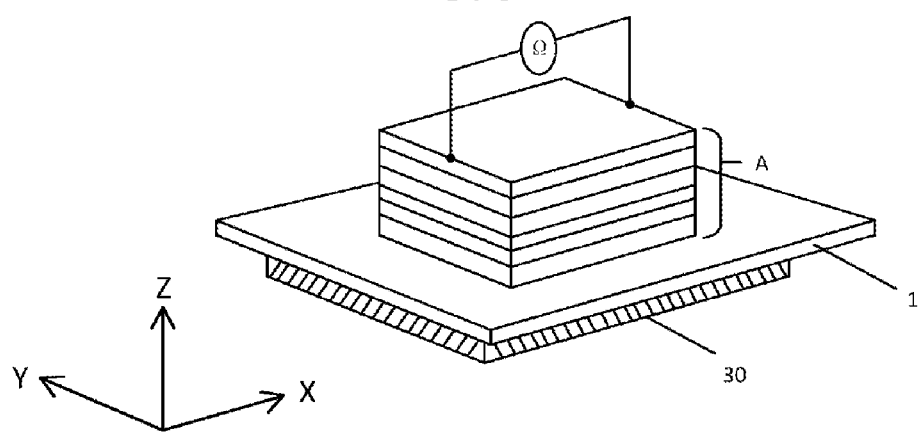
FIG. 4(a) is a schematic diagram of a position of a block permanent magnet relative to the magnetic multilayer thin film structure provided in an embodiment of the present disclosure.
Figure 4B:
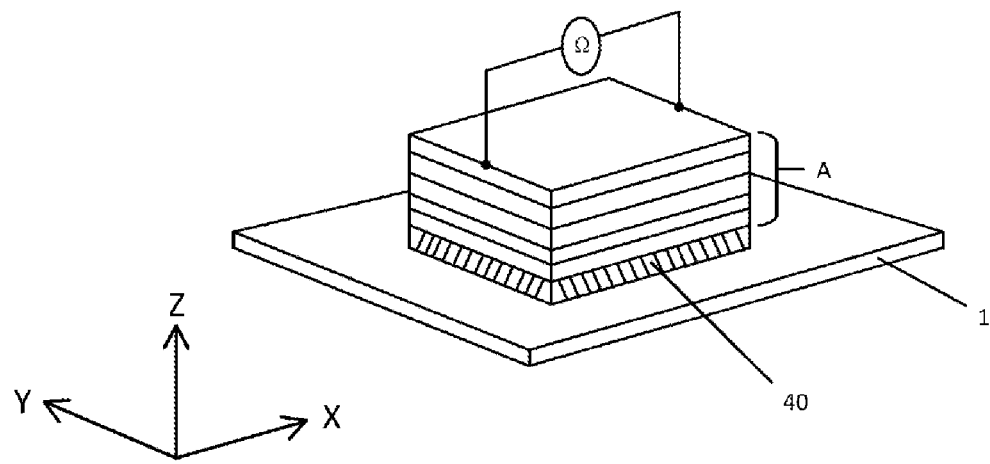
FIG. 4(b) is a schematic diagram of a position of a thin-film permanent magnet relative to the magnetic multilayer thin film structure provided in an embodiment of the present disclosure.
Figure 4C:
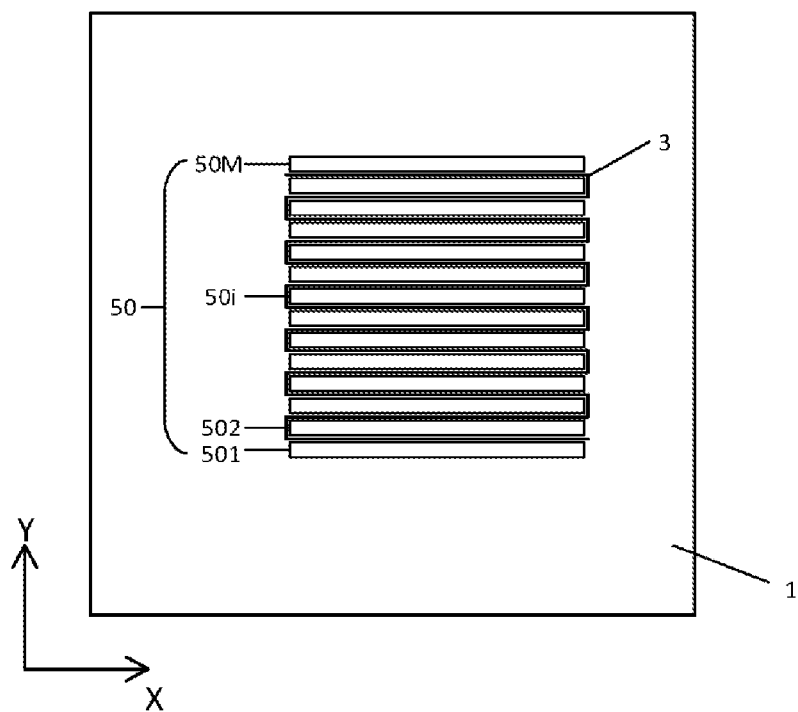
FIG. 4(c) is a schematic diagram of a relative position between a strip-shaped permanent magnet array and a serpentine strip circuit provided in an embodiment of the present disclosure.

In this embodiment, in order to make the deflection angle of the magnetic moment M of the ferromagnetic layer 13 within the X-Z plane within the preferred range, a permanent magnet on the X-Y plane may be additionally provided as needed. Types of the permanent magnet provided in this embodiment mainly include: the block permanent magnet located below the substrate 1. FIG. 4(a) is a schematic diagram of a position of a block permanent magnet relative to the magnetic multilayer thin film structure provided in an embodiment of the present disclosure. As shown in FIG. 4(a), the block permanent magnet 30 is located below the substrate 1, and the block permanent magnet 30 generates a magnetic field along a positive direction of a Z-axis. Alternatively, the types may include: a thin-film permanent magnet located between the substrate 1 and the magnetic multilayer thin film structure. FIG. 4(b) is a schematic diagram of a position of a thin-film permanent magnet relative to the magnetic multilayer film structure provided in an embodiment of the present disclosure. As shown in FIG. 4(b), the thin-film permanent magnet 40 is located between the substrate 1 and the magnetic multilayer thin-film structure A, and the thin-film permanent magnet 40 generates a magnetic field along the positive direction of the Z-axis. Alternatively, the types may include: a strip-shaped permanent magnet array located in a gap formed between the parallel line segments of the serpentine strip circuit. FIG. 4(c) is a schematic diagram of a relative position between a strip-shaped permanent magnet array and a serpentine strip circuit provided in an embodiment of the present disclosure. As shown in FIG. 4(c), the strip-shaped permanent magnet array 50 is located in the gap formed between the parallel line segments of the serpentine strip circuit, the strip-shaped permanent magnet array 50 includes a plurality of strip-shaped permanent magnets, and the strip-shaped permanent magnets generate a magnetic field along the positive direction of the Y-axis. Taking the magnetoresistive reference unit 3 as an example, the strip-shaped permanent magnet array 50 includes a plurality of strip-shaped thin-film permanent magnets 501, 502, . . . , 50i, . . . , 50M, where i is an integer smaller than M.

Figure 5:
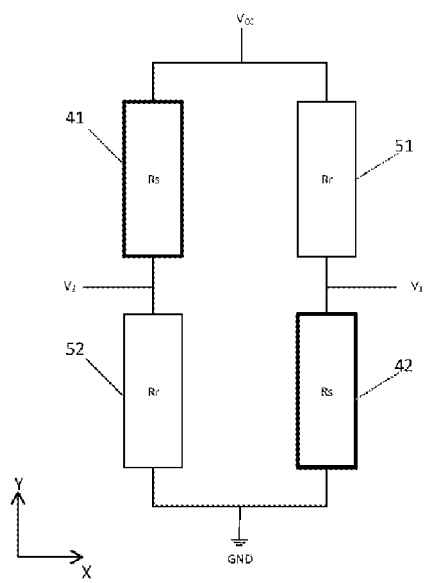
FIG. 5 is a schematic diagram of a full-bridge structure of the magnetoresistive hydrogen sensor provided in an embodiment of the present disclosure.

Further, the sensing arm 4 and the reference arm 5 may be interconnected to form a full bridge, a half bridge, or a quasi bridge. For example, FIG. 5 is a schematic diagram of a full-bridge structure of the magnetoresistive hydrogen sensor provided in an embodiment of the present disclosure. As shown in FIG. 5, a first end of a first sensing arm 41 is connected to a first end of a first reference arm 51, a second end of the first sensing arm 41 is connected to a first end of a second reference arm 52, a second end of the first reference arm 51 is connected to a first end of a second sensing arm 42, and a second end of the second reference arm 52 is connected to a second end of the second sensing arm 42.

Figure 6A:
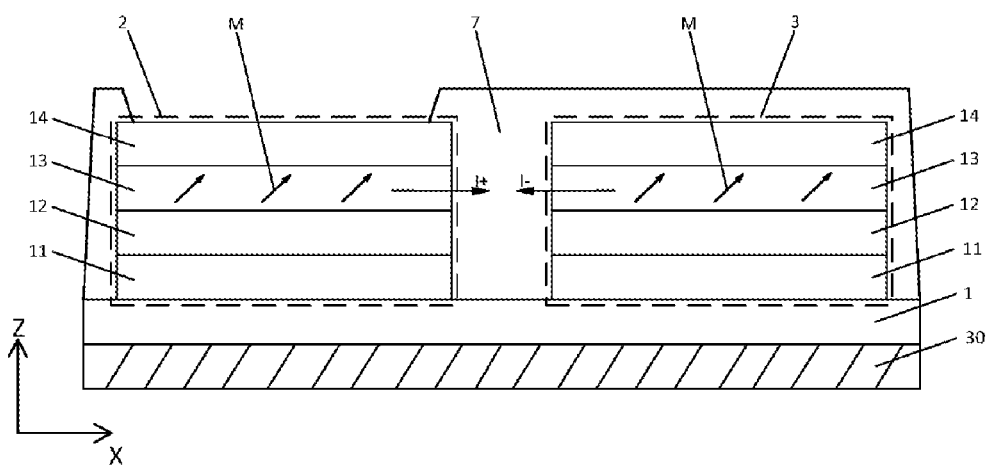
FIG. 6(a) is a schematic diagram of the magnetoresistive hydrogen sensor in the absence of hydrogen provided in an embodiment of the present disclosure.
Figure 6B:
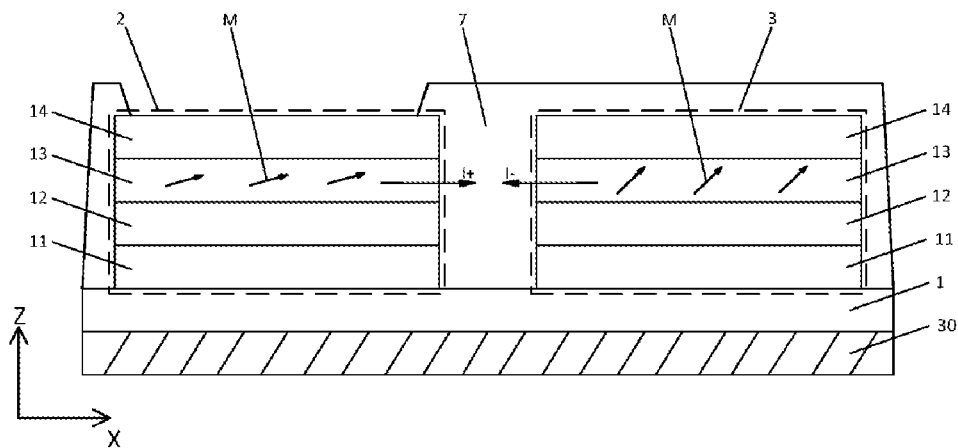
FIG. 6(b) is a schematic diagram of the magnetoresistive hydrogen sensor in the presence of hydrogen provided in an embodiment of the present disclosure.

FIG. 6(a) is a schematic diagram of the magnetoresistive hydrogen sensor in the absence of hydrogen provided in an embodiment of the present disclosure. FIG. 6(b) is a schematic diagram of the hydrogen sensor in the presence of hydrogen provided in an embodiment of the present disclosure. It should be noted that this embodiment is described using an example in which the magnetoresistive sensing unit 2 and the magnetoresistive reference unit 3 are AMR units having a same magnetic multilayer thin film structure.

Figure 7A:
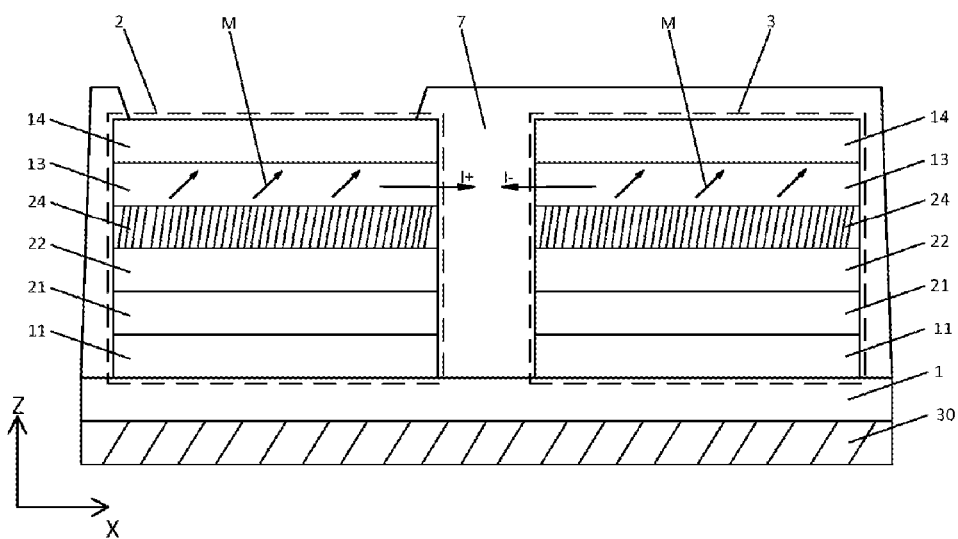
FIG. 7(a) is a schematic diagram of the magnetoresistive hydrogen sensor in the absence of hydrogen provided in an embodiment of the present disclosure.
Figure 7B:
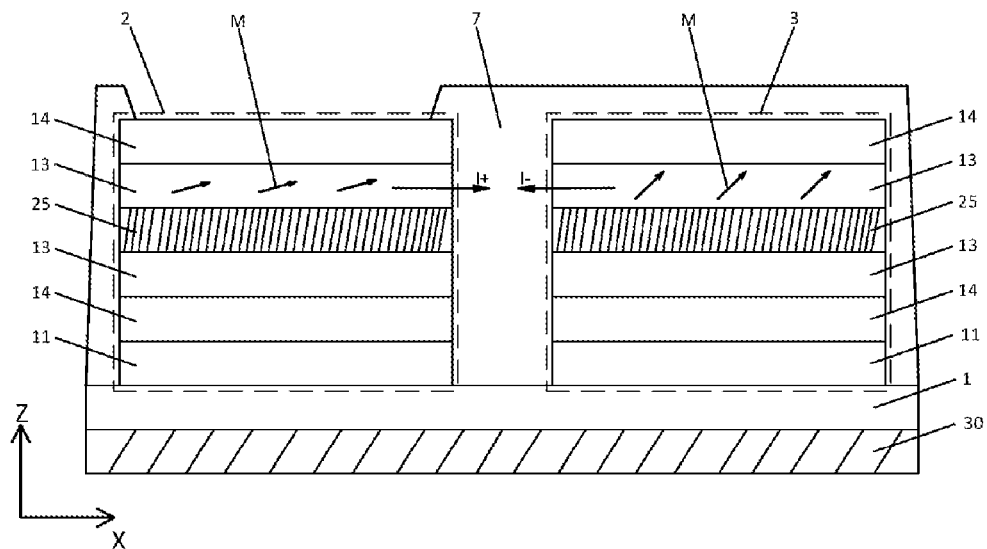
FIG. 7(b) is a schematic diagram of the magnetoresistive hydrogen sensor in the presence of hydrogen provided in an embodiment of the present disclosure.

FIG. 7(a) is a schematic diagram of the magnetoresistive hydrogen sensor in the absence of hydrogen provided in an embodiment of the present disclosure. FIG. 7(b) is a schematic diagram of the magnetoresistive hydrogen sensor in the presence of hydrogen provided in an embodiment of the present disclosure. It should be noted that this embodiment is described using an example in which the magnetoresistive sensing unit 2 and the magnetoresistive reference unit 3 are GMR spin valves having a same magnetic multilayer film structure.

Figure 8A:
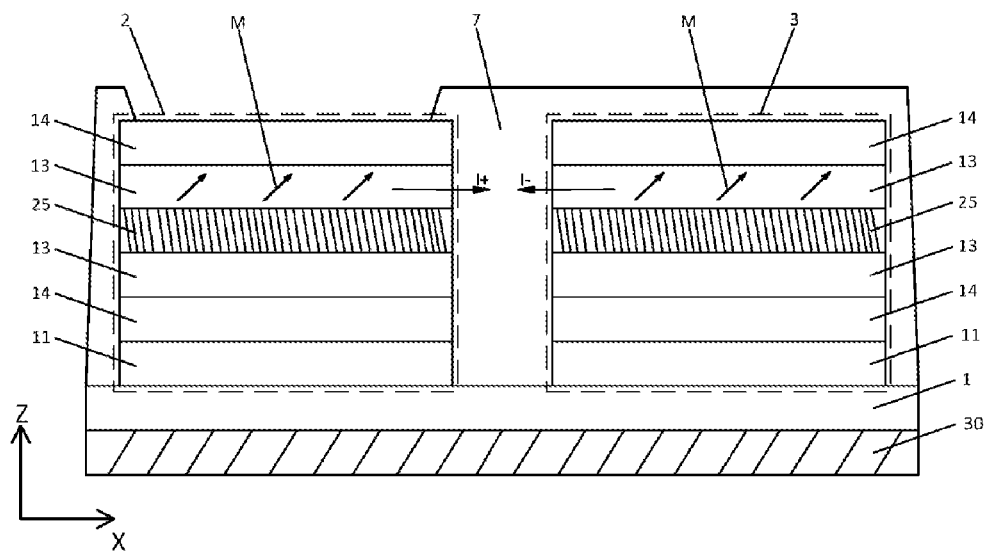
FIG. 8(a) is a schematic diagram of the magnetoresistive hydrogen sensor in the absence of hydrogen provided in an embodiment of the present disclosure.
Figure 8B:
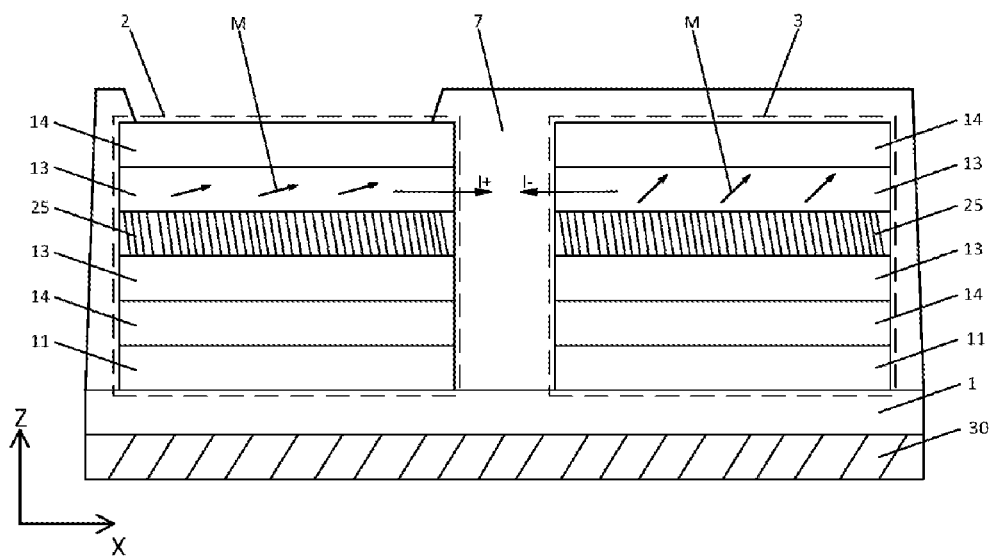
FIG. 8(b) is a schematic diagram of the magnetoresistive hydrogen sensor in the presence of hydrogen provided in an embodiment of the present disclosure.

FIG. 8(a) is a schematic diagram of the magnetoresistive hydrogen sensor in the absence of hydrogen provided in an embodiment of the present disclosure. FIG. 8(b) is a schematic diagram of the magnetoresistive hydrogen sensor in the presence of hydrogen provided in an embodiment of the present disclosure. It should be noted that this embodiment is described using an example in which the magnetoresistive sensing unit 2 and the magnetoresistive reference unit 3 are GMR multilayer film stacks having a same magnetic multilayer thin film structure.

The working principle of the magnetoresistive hydrogen sensor of the present disclosure is briefly described with reference to FIG. 6(a), FIG. 6(b), FIG. 7(a), FIG. 7(b), FIG. 8(a), and FIG. 8(b). When hydrogen is absent in an external environment, in the magnetoresistive sensing unit 2, a resistance of the Pd layer 14 located on the top of the magnetic multilayer thin film structure is R0, an angle between the magnetic moment M of the ferromagnetic layer 13 below and current I+ is θ, an anisotropic magnetoresistance of the ferromagnetic layer 13 is $\Delta R \cos^2\theta$, and a total resistance RS of the magnetoresistive sensing unit 2 is $R_s = R_0 + \Delta R \cos^2\theta$.

In the magnetoresistive reference unit 3, a resistance of the Pd layer 14 located on the top of the magnetic multilayer thin film structure is R0, an angle between the magnetic moment M of the ferromagnetic layer 13 below and current I− is π−θ, an anisotropic magnetoresistance of the ferromagnetic layer 13 is $\Delta R \cos^2(\pi-\theta) = \Delta R \cos^2\theta$, and a total resistance Rr of the magnetoresistive reference unit 3 is $R_r = R_0 + \Delta R \cos^2\theta$. Thus, a voltage signal output is $$V_{out} = V_2 - V_1 = \frac{R_S - R_r}{R_S + R_r} V_{cc} = 0.$$

When hydrogen is present in the environment, in the magnetoresistive sensing unit 2, the Pd layer 14 located on the top of the magnetic multilayer thin film structure absorbs hydrogen and then expands, and its resistance increases to $R_0'$. At the same time, perpendicular magnetic anisotropy induced by the Pd layer 14 on the top of the magnetic multilayer thin film structure in the ferromagnetic layer 13 below also changes, such that the magnetic moment M of the ferromagnetic layer 13 rotates within an X-Z plane, the rotation angle AO positively correlates to the hydrogen concentration, the angle between the magnetic moment M and the current I+ becomes $\theta' = \theta - \Delta\theta$, and the anisotropic magnetoresistance of the ferromagnetic layer 13 increases to $\Delta R \cos^2\theta'$. Therefore, a total resistance $R_s'$ of the magnetoresistive sensing unit 2 is $R_s' = R_0' + \Delta R \cos^2\theta'$.

In the magnetoresistive reference unit 3, since the passivating insulation layer 7 blocks hydrogen, the total resistance Rr of the magnetoresistive reference unit 3 remains unchanged, and is still $R_r = R_0 + \Delta R \cos^2\theta$.

Thus, a voltage signal output is:

$$V'_{out} = V'_2 - V'_1 = \frac{R'_S - R_r}{R'_S + R_r} V_{cc} = \frac{(R'_0 - R_0) + \Delta R(\cos^2\theta' - \cos^2\theta)}{(R'_0 + R_0) + \Delta R(\cos^2\theta' + \cos^2\theta)} V_{cc}.$$

Figure 9:
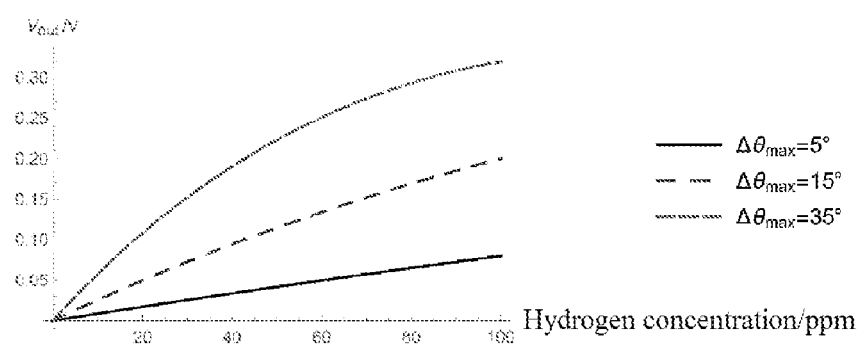
FIG. 9 is a schematic diagram between hydrogen concentration and output voltage of the hydrogen sensor under different $\Delta\theta_{max}$ conditions provided in this embodiment.

The maximum value of $\theta'' = \theta - \Delta\theta$ is denoted as $\Delta\theta_{max}$. $\Delta\theta_{max}$ depends on the material and thickness of a thin film in the magnetic multilayer thin film structure, and is also affected by the order of thin film stacking. FIG. 9 is a schematic diagram between hydrogen concentration and output voltage of the hydrogen sensor under different $\Delta\theta_{max}$ conditions provided in this embodiment, to more intuitively show the effect of detecting external hydrogen concentration using the magnetoresistive hydrogen sensor of the present disclosure. Further, a relationship between hydrogen concentration and output voltage of the hydrogen sensor when $\Delta\theta_{max}$ is 50, 150 and 350 is shown in FIG. 9. As can be seen from FIG. 9, the higher the $\Delta\theta_{max}$ is, the better the hydrogen concentration detection effect of the hydrogen sensor is.

The magnetoresistive hydrogen sensor provided in embodiments of the present disclosure includes: a substrate located on an X-Y plane; magnetoresistive sensing units and magnetoresistive reference units located on the substrate, the magnetoresistive sensing units being electrically connected to form a sensing arm, the magnetoresistive reference units being electrically connected to form a reference arm, the sensing arm and the reference arm being electrically interconnected to form a referenced bridge structure; wherein the magnetoresistive sensing units and the magnetoresistive reference units are AMR units having a same magnetic multilayer thin film structure, or GMR spin valves or GMR multilayer film stacks having a same magnetic multilayer thin film structure. The magnetic multilayer thin film structure is made into a serpentine strip circuit by a semiconductor micromachining process, and the magnetoresistive reference unit is covered with a passivating insulation layer. The present disclosure has very favorable temperature compensation and high sensitivity, and has the advantages of small size, low power consumption, wide detection range of hydrogen concentration, and the like.

On the basis of the above embodiments, an embodiment of the present disclosure further provides a method for detecting a hydrogen concentration using the above magnetoresistive hydrogen sensor, including:

placing the hydrogen sensor in a hydrogen-containing gas environment, absorbing hydrogen by the Pd layer covering the magnetoresistive sensing units to change perpendicular magnetic anisotropy of the ferromagnetic layers in the magnetic multilayer thin film structures of the magnetoresistive sensing units, such that the magnetic moment of the ferromagnetic layer rotates to produce a magnetoresistance value change that positively correlates to the hydrogen concentration;

obtaining an output voltage value change of a bridge structure based on the magnetoresistance value change, and detecting the hydrogen concentration based on the output voltage value change of the bridge structure.

The above description only provides preferred embodiments of the present disclosure. All other embodiments obtained by those of ordinary skills in the art based on the embodiments of the present disclosure without making creative work fall within the scope of protection of the present disclosure. It should be pointed out that those of ordinary skills in the art may further make some improvements and modifications without departing from the principle of the present disclosure. These improvements and modifications should also be regarded as the scope of protection of the present disclosure.

The invention claimed is:

1. A magnetoresistive hydrogen sensor, comprising:
   a substrate located on an X-Y plane; and
   magnetoresistive sensing units and magnetoresistive reference units located on the substrate, the magnetoresistive sensing units being electrically connected to form a sensing arm, the magnetoresistive reference units being electrically connected to form a reference arm, the sensing arm and the reference arm being electrically interconnected to form a referenced bridge structure; wherein the magnetoresistive sensing units and the magnetoresistive reference units are AMR units having a same magnetic multilayer thin film structure, or GMR units having a same magnetic multilayer thin film structure; the magnetoresistive sensing units and the magnetoresistive reference units are respectively covered with a Pd layer, and a passivating insulation layer further covers over the Pd layer covering the magnetoresistive reference units;
   wherein the magnetic multilayer thin film structure is made into a serpentine strip circuit by a semiconductor micromachining process, a parallel line segment of the serpentine strip circuit follows an X direction, a corner of the serpentine strip circuit follows a Y direction, a gap is formed between adjacent parallel line segments of the serpentine strip circuit, a long axis of the gap follows the X direction, a short axis of the gap follows the Y direction; and the semiconductor micromachining process includes, but is not limited to, a photoetching technology and an ion etching technology;
   wherein the Pd layer covering the magnetoresistive sensing units absorbs hydrogen to change magnetic anisotropy of ferromagnetic layers in the magnetoresistive sensing units; the passivating insulation layer isolates hydrogen to avoid changing magnetic anisotropy of ferromagnetic layers in the magnetoresistive reference units; and a hydrogen concentration is detected based on an output voltage value change of the referenced bridge structure before and after absorbing hydrogen.

2. The magnetoresistive hydrogen sensor according to claim 1, wherein the GMR unit is a GMR spin valve, the magnetic multilayer thin film structure comprises from bottom to top: a seed layer, an antiferromagnetic layer, a PMA ferromagnetic layer, a buffer layer, a Cu spacer layer, a buffer layer, a ferromagnetic layer, a composite intermediate layer, and a Pd layer, or comprises from top to bottom: a seed layer, a PMA interface layer, a PMA ferromagnetic layer, a buffer layer, a Cu spacer layer, a buffer layer, a ferromagnetic layer, and a composite intermediate layer; wherein the composite intermediate layer is [PMA interface layer/ferromagnetic layer]$_m$, m being an integer;
or when the GMR unit is a GMR multilayer film stack having interlayer antiferromagnetic coupling, the magnetic multilayer thin film structure comprises from bottom to top: a seed layer and a multi-film intermediate layer; wherein the multi-film intermediate layer is [ferromagnetic layer/non-magnetic intermediate layer/ferromagnetic layer]$_p$, p being an integer.

3. The magnetoresistive hydrogen sensor according to claim 1, wherein a block permanent magnet is provided below the substrate, and the block permanent magnet generates a magnetic field along a positive direction of a Z-axis;
or, a thin-film permanent magnet is provided between the substrate and the bridge structure, and the thin-film permanent magnet generates a magnetic field along the positive direction of the Z-axis;
or, a strip-shaped permanent magnet array is provided above or below the serpentine strip circuit, and the strip-shaped permanent magnet array comprises a plurality of strip-shaped permanent magnets arranged between the gap between the parallel line segments of the serpentine strip circuit and generating a magnetic field along a positive direction of a Y-axis.

4. The magnetoresistive hydrogen sensor according to claim 1, wherein the referenced bridge structure comprises a half-bridge structure, a full-bridge structure, or a quasi-bridge structure.

5. The magnetoresistive hydrogen sensor according to claim 1, wherein a material of the substrate includes, but is not limited to, one of Si, SiO$_2$, or fused silica, and a material of the passivating insulation layer includes, but is not limited to, one of photoresist, Al$_2$O$_3$, or SiN.

6. A method for detecting a hydrogen concentration using the magnetoresistive hydrogen sensor according to claim 1, comprising:
placing the hydrogen sensor in a hydrogen-containing gas environment, absorbing hydrogen by the Pd layer covering the magnetoresistive sensing units to change perpendicular magnetic anisotropy of the ferromagnetic layers in the magnetic multilayer thin film structures of the magnetoresistive sensing units, such that the magnetic moment of the ferromagnetic layer rotates to produce a magnetoresistance value change that positively correlates to the hydrogen concentration; and
obtaining an output voltage value change of a bridge structure based on the magnetoresistance value change, and detecting the hydrogen concentration based on the output voltage value change of the bridge structure.

7. The magnetoresistive hydrogen sensor according to claim 1, wherein the magnetic multilayer thin film structure of the AMR unit comprises from bottom to top:
a seed layer; and
a composite intermediate layer;
wherein the composite intermediate layer is [PMA interface layer/ferromagnetic layer]$_n$, n being an integer.

8. The magnetoresistive hydrogen sensor according to claim 7, wherein an easy axis of the ferromagnetic layer is perpendicular to an X-Y plane, a magnetic moment of the ferromagnetic layer deflects towards an adjacent Pd layer within an X-Z plane within an angle range of 10°-80°, the ferromagnetic layer is made of a magnetostrictive material, including but not limited to one of single elements of Fe, Co, or Ni, or one of alloys of CoFe, NiFe, CoPt, CoPd, CoFeB, or NiFeCo, a material of the seed layer includes, but is not limited to, one of Ta or W, and a material of the PMA interface layer includes, but is not limited to, one of magnesium oxide, palladium oxide, or platinum oxide.

9. The magnetoresistive hydrogen sensor according to claim 8, wherein a material of the PMA ferromagnetic layer includes, but is not limited to, one of Co or CoFeB, a material of the buffer layer includes, but is not limited to, one of Ta or Ru, and a material of the non-magnetic intermediate layer includes, but is not limited to, one of Cu, Ru, Pd, Cr, Au, or Ag.

* * * * *